US006823264B1

(12) United States Patent
Hauge

(10) Patent No.: US 6,823,264 B1
(45) Date of Patent: Nov. 23, 2004

(54) METHOD AND SYSTEM FOR MEASURING DEPTH TO SATURATED SOILS

(76) Inventor: Odd Hauge, 11844 NE. 90th St., Kirkland, WA (US) 98033-5814

( * ) Notice: Subject to any disclaimer, the term of this patent is extended or adjusted under 35 U.S.C. 154(b) by 0 days.

(21) Appl. No.: 10/198,056

(22) Filed: Jul. 17, 2002

Related U.S. Application Data

(60) Provisional application No. 60/306,180, filed on Jul. 17, 2001.

(51) Int. Cl.$^7$ .......................... G06F 19/00; G01N 5/02
(52) U.S. Cl. ............................................. 702/6; 73/73
(58) Field of Search .................... 702/6; 73/73, 170.18

(56) References Cited

U.S. PATENT DOCUMENTS 5,941,121 A * 8/1999 Faybishenko .................. 73/73
6,263,726 B1 * 7/2001 Hubbell et al. ................ 73/73

OTHER PUBLICATIONS

"Regressive Modeling of Soil Water Table Fluctuations", Boucneau et al., Mathematics and Computers in Simulation 42 (1996), Elsevier, pp. 271–277.*

"Maximum Rate of Upward Flow from Water Tables", Arbhabhirama et al., Conference on Hydraulic and Fluid Mechanics, Sidney, 1968, Paper No. 2617.*

* cited by examiner

*Primary Examiner*—John Barlow
*Assistant Examiner*—Toan M. Le
(74) *Attorney, Agent, or Firm*—Christensen O'Connor Johnson Kindness pllc

(57) ABSTRACT

A method is provided for determining the depth to the saturated soil at a selected site. A first and second instance wherein the depth of the water table equals the depth to the saturated soil is identified (142). The rate of change of the depth to the saturated soil is calculated (146) as a function of the specific yield, amount of time between the instances, total precipitation occurring between the instances, and depth of the water table at each instance. Then, the depth to the saturated soil for a third instance is calculated (148) as a function of the rate of change of the depth to the saturated soil. The calculated depth to the saturated soil for a third instance may be adjusted as a function of precipitation occurring at the site.

46 Claims, 12 Drawing Sheets

METHOD AND SYSTEM FOR MEASURING DEPTH TO SATURATED SOILS

CROSS-REFERENCE(S) TO RELATED APPLICATION(S)

This application claims the benefit of prior U.S. Provisional Patent Application No. 60/306,180, filed on Jul. 17, 2001, priority from the filing date of which is hereby claimed under 35 U.S.C. §119.

FIELD OF THE INVENTION

The invention relates to methods of determining the depth to saturated soils and more particularly to using that information to determine whether a particular site is a wetland.

BACKGROUND OF THE INVENTION

Wetlands may include marshes, bogs, and swamps. Wetland delineations tend to be controversial because such a determination often pits the interest of environmental protectionists against the interests of landowners. Therefore, standards or guidelines have been created to standardize wetland delineations. These guidelines also attempt to balance the interests of the public and private landowner. According to typical guidelines, whether a particular parcel of land qualifies as a wetland generally depends upon the percentage of the growing season that the surface of the soil is continuously saturated with water.

One example of wetland delineation guidelines includes the Corps of Engineers' Wetlands Delineation Manual of January 1987 ("'87 Manual"). The '87 Manual provides guidelines that may be used to determine whether a particular parcel of land is a wetland. Generally, land qualifies as a wetland if it is continuously saturated to the surface between 5% and 12.5% of the growing season. However, the '87 Manual indicates that many sites are not wetlands despite being continuously saturated to the surface between 5% to 12.5% of the growing season. A delineation in these cases is left to the judgment of the delineator. According to the '87 Manual, sites not continuously saturated at least 5% of the growing season are not wet enough to be considered wetlands.

The '87 Manual provides that, delineators (persons who determine whether a site is a wetland) may consider three parameters, soil characteristics, vegetation, and hydrology, when evaluating whether a site is a wetland. Soil characteristics may be used to determine whether the soils at the site are hydric soils. Hydric soils form under conditions of saturation including flooding that persists long enough to develop anaerobic conditions in the soil. These anaerobic conditions, characteristic of hydric soils, may be observed as color changes in the soils.

The hydrology determination, i.e., the depth to saturation in the soil, is the most controversial determination because a delineator cannot directly observe the hydrologic condition of the ground. Therefore, the delineator must rely on other indicators such as vegetation and soil characteristics to make the hydrology determination. Accurately evaluating the site in this manner requires numerous visits to the site. However, it is not uncommon for a delineator to make a delineation based on only a single visit. After the hydrology determination is made, it may be compared with standard hydrological criteria, such as those found in the '87 Manual.

Digging a pit in the ground and measuring the depth at which water appears in the pit will yield the depth of the water table (the upper boundary of a free groundwater body at atmospheric pressure). However, the depth of the upper boundary of saturated soil (referred to hereafter as the depth to the saturated soil) is not necessarily equal to the depth of the water table. Capillary action, described in more detail below, may draw water up through the grains of soil to a level above the water table causing saturated soil to occur above the water table. The volume of water located between the depth to the saturated soil and the water table is known as the capillary fringe. Both the depth to the saturated soil and the water table may rise during rainfall and shrink when depletion mechanisms such as drainage, evaporation, and transpiration deplete water from the soil.

Referring FIGS. 1A–1E, the capillary fringe will be explained in greater detail. FIG. 1A depicts a barrel 10 of soil grains 14 and water 12. In FIG. 1A, the water 12 extends above the top surface of the soil grains 14. Because the water table 16 extends above the surface of the soil, there is no capillary tension. FIG. 1B depicts barrel 10 after water 12 has been depleted from the barrel 10 to the point that the depth to the saturated soil and the water table 16 are at the top of the surface of the soil grains 14. Therefore, there is no capillary fringe.

FIG. 1C depicts barrel 10 after one additional drop of water has been depleted from the barrel depicted in FIG. 1B. Menisci 20 form between soil grains 14 at the surface of the soil. As can be seen in FIG. 1C, the water table 16 has dropped to well below the surface of the soil while the depth to the saturated soil remains at the surface of the soil. Each menisci 20 has water 12 on one side and air on the other. Because the water 12 is attracted to the soil grains 14, the water 12 relentlessly seeks to encompass more soil grains 14. Capillary forces draw the water 12 upward to the surface of the soil forming a zone of negative pressure, known as a capillary fringe 22, between the depth to the saturated soil and the water table 16. The surface of the capillary fringe 22 is formed by menisci 20. The surface of the capillary fringe 22 may also be referred to as the capillary front. The capillary fringe 22 is depicted as a gray area between the water table and the surface of the soil. The capillary fringe 22 will move upward until negative pressure behind it reaches the maximum the menisci 20 can support. In this manner, the capillary forces create a pressure differential across the menisci 20 between the saturated soil and the air above the menisci 20. Above the menisci 20, the pressure is atmospheric. Below the menisci 20, the pressure may be as low as minus 12 inches of water. The negative pressure along the surface of the soil makes a visual observation of the depth to the saturated soil difficult because the surface of the soil may appear dry despite the fact that the soil grains directly underneath the surface grains are fully saturated with water.

FIG. 1D depicts barrel 10 after an additional drop of water has been depleted. In this figure, the water table 16 has fallen to the maximum distance the menisci 20 will support. This is evidenced by the fact that air entry 26 has occurred at the surface of the soil. Because the negative pressure between the menisci 20 and the water table is at its maximum, as the water table drops, it will pull the depth to the saturated soil downward with it. Under the conditions depicted in FIG. 1O, the capillary fringe 22 is at its maximum length, which may be as large as approximately 12 inches of water. Again, the negative pressure along the surface of the soil will make the soil appear dry despite the fact that ground remains saturated to the surface of the soil.

Further water depletion from the barrel, as depicted in FIG. 1E will produce a non-saturated condition at the surface of the soil. Under these conditions, the depth to the saturated soil (i.e., depth to the surface of the capillary fringe 22), and the water table 16 will change depths at the same time separated by the full extent of the capillary fringe 22 (up to 12 inches).

Specific yield is the fraction of the saturated soil consisting of water that will drain by gravity when the water table drops. The magnitude of the drop in the depth to the saturated soil from FIG. 1D to FIG. 1E is a function of the specific yield of the soil contained in barrel 10.

In FIGS. 1A through 1E, as water was depleted from the barrel 10, no additional water was added. Of course, this is generally not the case in the field. When water is added, such as by precipitation, the surface of the capillary fringe becomes disturbed when new water fills in the menisci and relaxes the tension between the surface of the capillary fringe and the water table. When the tension is relaxed, the pressure in the area of negative pressure increases to atmospheric and the water table moves upward to the depth to the saturated soil. Under these circumstances, the water table and saturated soils may occur at the same depth which may be above, at, or below the surface of the soil. When the rain ends and the excess surface water has been depleted, the volume of water in the saturated soil decreases restoring the tension between the depth to the saturated soil and the water table.

Referring to FIG. 2, an idealized hydrograph 40 of a wetland can be viewed. Arrow 42 depicts time increasing from the left-hand side to the right-hand side of FIG. 2. In this figure, the capillary fringe 50 spans the distance between the surface of the soil 44 and the water table 48. A period of rain starting at time 54 and ending at time 56 causes the water table 48 to move upward to a location above the surface of the soil 44 creating a volume of water 58 above the surface of the soil 44. At this period of time, the capillary fringe collapses. After the period of rain, water is depleted. Water may be depleted by depletion mechanisms such as drainage, evaporation, and/or transpiration. When sufficient water has depleted, the water table 48 drops in depth and the capillary fringe 50 is reformed. However, the depth to the saturated soil 46 remains at the surface of the soil 44 with the capillary fringe 50 spanning the distance between the surface of the soil 44 and the water table 48. Therefore, FIG. 2 depicts a site where the surface of the soil is continuously saturated with water such as certain types of wetlands.

Referring to FIG. 3, an idealized hydrograph 80 of an upland site may be viewed. Arrow 82 depicts time increasing from the left-hand side to the right-hand side of FIG. 3. Initially, both the water table 88 and the depth to the saturated soil 86 are separated by the capillary fringe 90. Both surfaces continuously drop until the start 94 of a period of rain when the capillary fringe 90 collapses and both the depth to the saturated soil 86 and the water table 88 rise to the surface of the soil 84. As water is added, surface water 98 is appears above the surface of the soil 84. Shortly after the end 96 of the period of rain, water is depleted by depletion mechanisms such as drainage, evaporation, and/or transpiration. As a result of the depletion of water, the water table 88 drops and the capillary fringe 90 is reformed. The capillary fringe 90 maintains the depth to the saturated soil 86 at the surface of the soil 84 only briefly. As the water table 88 drops, the depth to the saturated soil 86 also drops. Therefore, in this idealized depiction of uplands, the depth to the saturated soil reaches the surface of the soil only during periods of precipitation and for a short time thereafter.

In summary, the capillary fringe causes the depth to the saturated soil to be as much a 12 inches above the water table. As mentioned above, the depth of the water table can be determined by the depth at which water occurs in a pit dug into the ground. Such a pit is typically 18 inches deep. However, the depth to the saturated soil cannot be accurately determined in this manner because the membrane of menisci and soil grains forming the surface of the capillary fringe may follow the wall of the pit holding water in the soil and preventing water from entering the pit. Under these circumstances, water will not seep into the pit from the saturated soil so long as the negative pressure of the capillary fringe opposes the seepage of water into the pit. Furthermore, the negative pressure along the pit wall obscures visual observation of the saturated soils (i.e., the soil along the pit wall adjacent to the saturated soils will appear dry despite the fact that the soil behind it is saturated with water). Determining which sites are wetlands is therefore complicated because determining the depth to the saturated soil is difficult.

One method of directly measuring the depth to the saturated soil involves using a tensiometer to measure suction or tension in the soil. This method works by using the tensiometer to determine the depth at which the pressure in the soil changes from atmospheric to below atmospheric (i.e., negative pressure). However, this method has the drawback of requiring blind searching to locate the depth to the saturated soil.

Determining the depth to the saturated soil is useful in determining whether a site qualifies as a wetland. The depth to the saturated soil can be used to determine the duration of continuous saturation at the surface of the soil. The duration of continuous saturation at the surface of the soil can be compared with wetland standards, such as those found in the '87 Manual, to determine whether a particular site should be considered a wetland.

It is clear from the above discussion of the capillary fringe that a determination of the depth of the water table alone is insufficient to determine the depth to the saturated soil. Therefore, a need exists for a more accurate method of determining the depth to the saturated soil in the ground. Further, a need exists for a system capable of performing such a method.

SUMMARY OF THE INVENTION

The present invention provides a method of determining the depth to the saturated soil in the ground at a selected site. In one embodiment, the method includes identifying a first and second instance wherein the depth of the water table equals the depth to the saturated soil at the selected site. The second instance preferably occurs after the first instance. Next, the method determines the depth of the water table at the first and second instances and the total precipitation that occurred between the first and second instances. The rate of change of the depth to the saturated soil may be calculated as a function of the specific yield for the selected site, the amount of time between the instances, the total precipitation that occurred between the instances, and the depth of the water table at each instance.

With this information, the depth to the saturated soil for a third instance may be calculated. After selecting a third instance, the depth to the saturated soil for the third instance may be calculated as a function of the rate of change of the depth to the saturated soil. Further, the total amount of precipitation occurring on the third instance and the total precipitation that occurred between the first and third instances may be determined so that the depth to the saturated soil may be adjusted for the third instance as a function of the total precipitation that occurred between the first and third instances and the total amount of precipitation occurring on the third instance. If the third instance occurs after the second instance, the depth to the saturated soil may be adjusted for the third instance as a function of the total precipitation that occurred between the second and third instances and the total amount of precipitation occurring on the third instance.

As another aspect of the present invention, the rate of change of the depth to the saturated soil may be correlated with factors that affect water depletion. This correlation may yield one or more depletion characteristics of a site that may be used to improve the determination of the depth to the saturated soil. Specifically, the rate of change of the depth to the saturated soil may be correlated with the factors that effect water depletion to improve the determination of the depth to the saturated soil at the third instance and/or an instance not between the first and second instances.

A system and computer-readable medium capable of performing actions generally consistent with the method above represent further aspects of the present invention.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

Figure 1E:
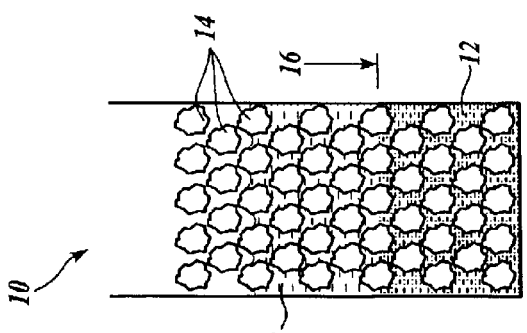
FIGS. 1A–E are illustrations of a barrel containing soil grains and water demonstrating the impact of depleting water from the barrel on the depths of both the saturated soil and water table.
Figure 1D:
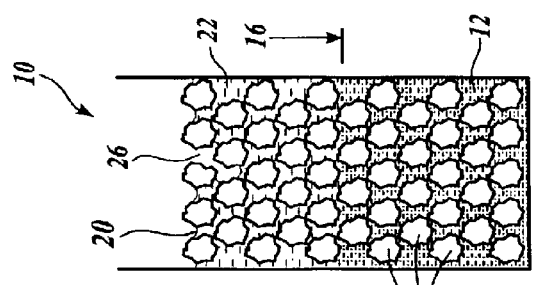
Figure 1C:
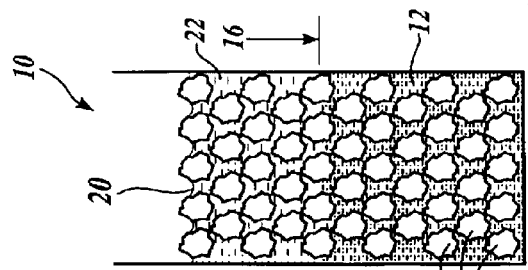
Figure 1B:
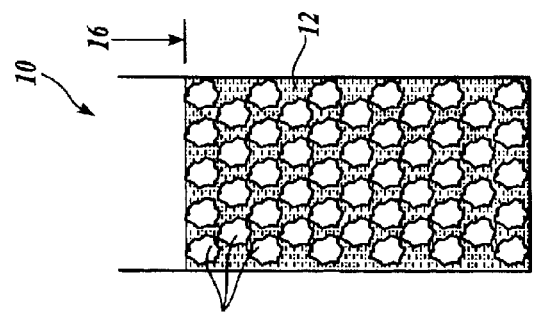
Figure 1A:
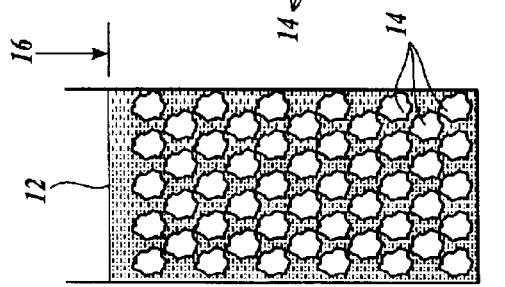
Figures 2, 3:
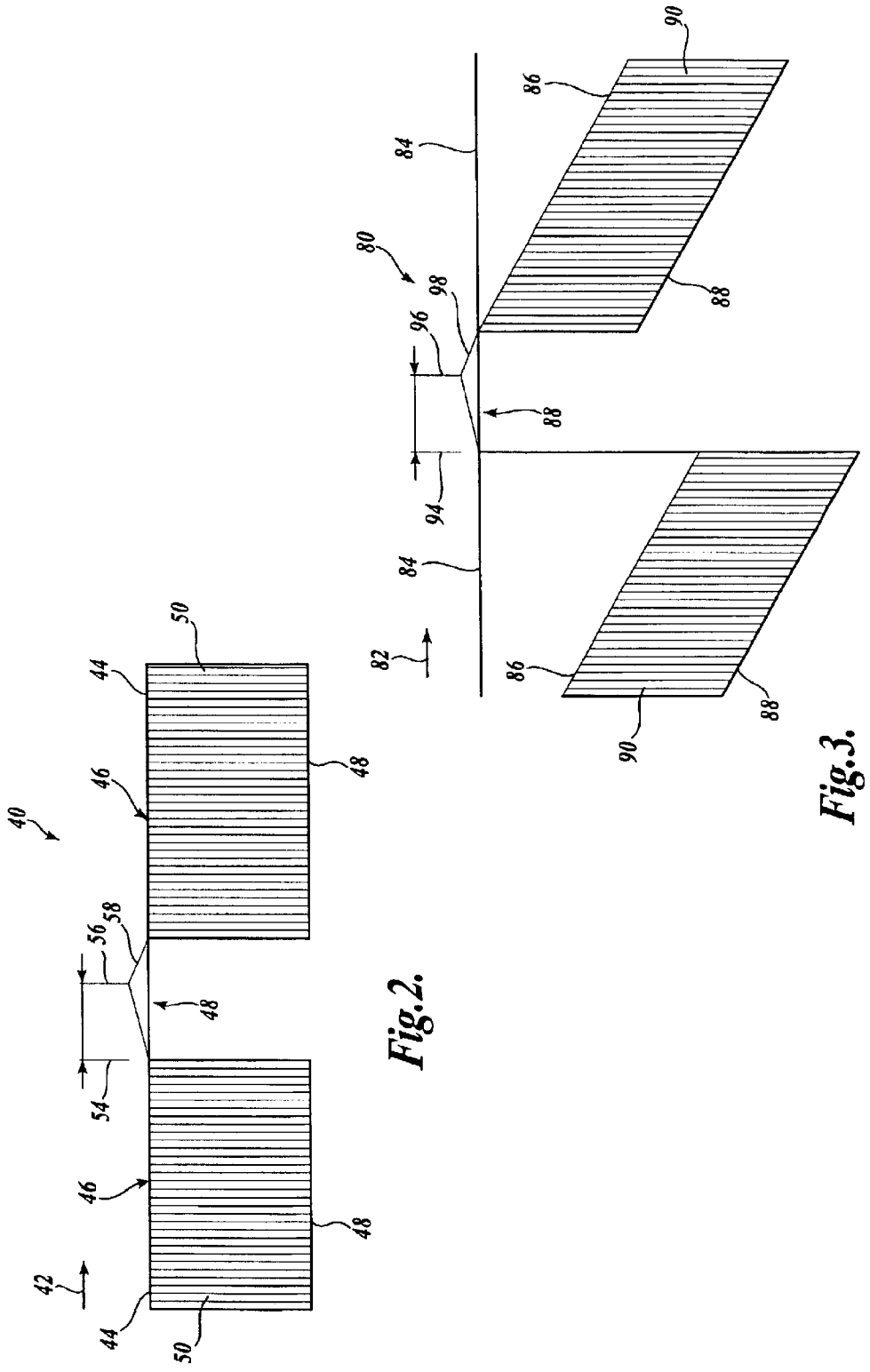
FIG. 2 is an idealized hydrograph of a wetland.
FIG. 3 is an idealized hydrograph of an upland.
Figure 4:
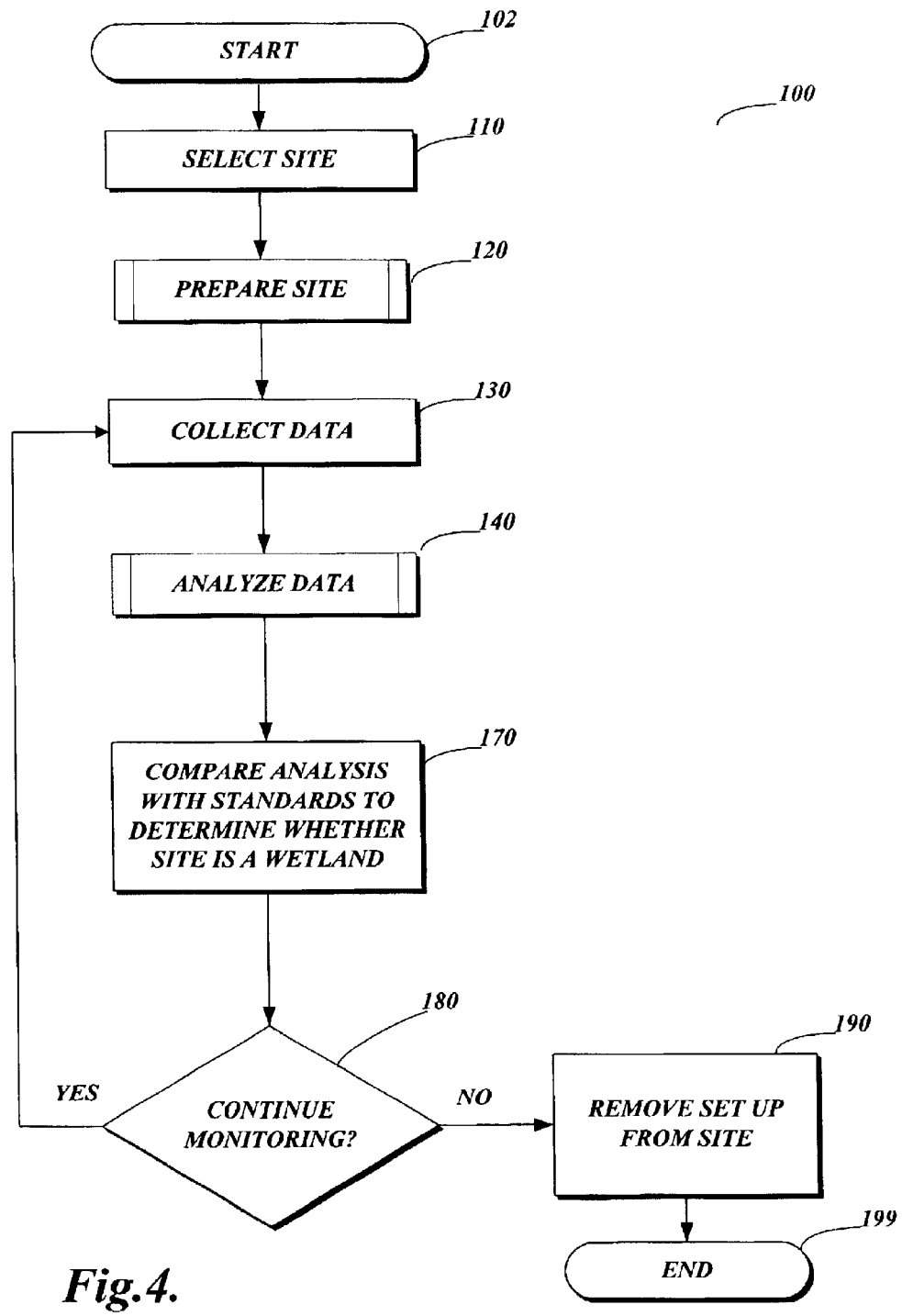
FIG. 4 is a flow diagram illustrative of a method for determining the depth to the saturated soil at a particular site in accordance with the present invention.

In one aspect of the present invention, a method 100 for determining the depth to the saturated soil at a particular site, is depicted in FIG. 4. Method 100 starts at block 102. In block 110, a site is selected at which the depth to the saturated soil is to be measured. Next, at block 120, the site is prepared or properly set up to record measurements necessary to determine the depth to the saturated soil.

Figure 5:
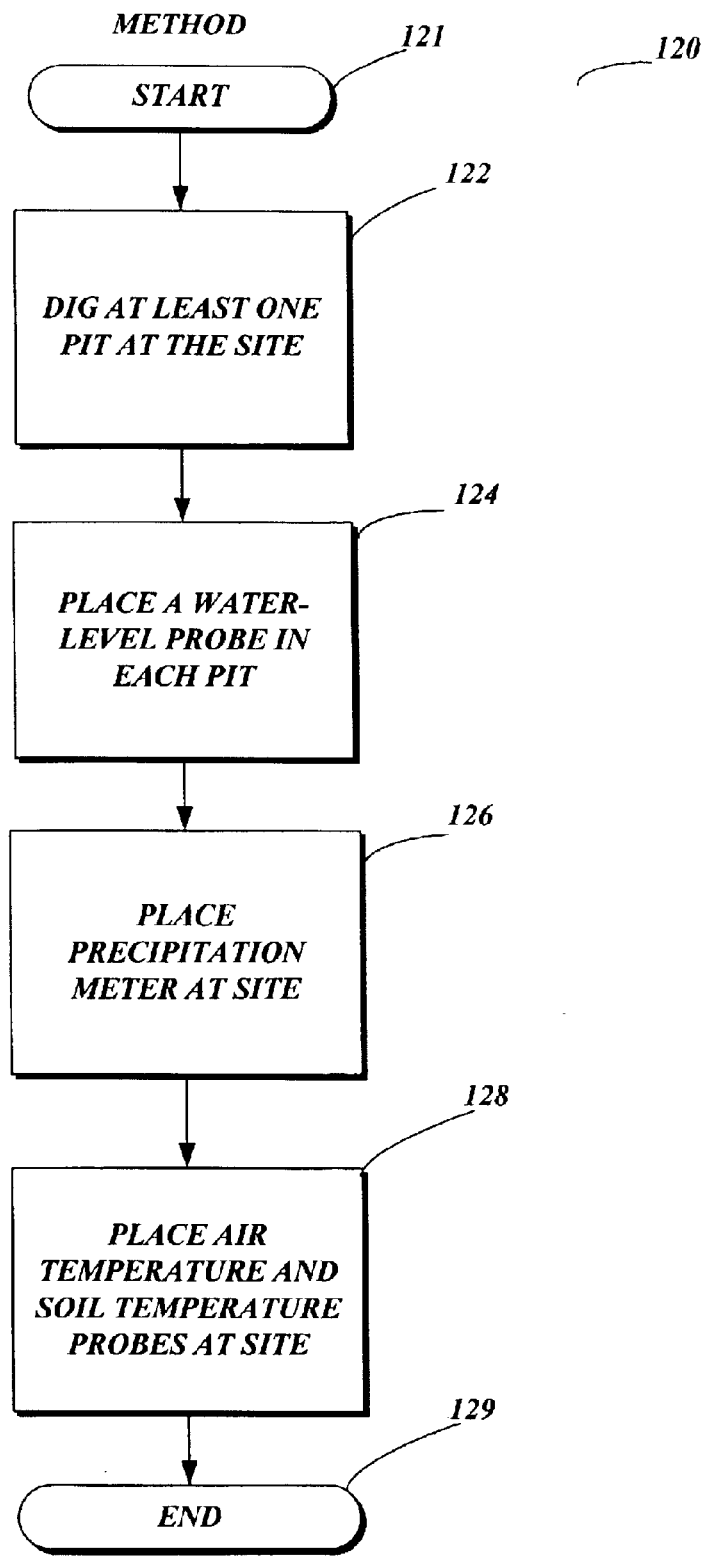
FIG. 5 is a flow diagram illustrative of a method of preparing a site for data collection to determine the depth to the saturated soil at the site in accordance with the method of FIG. 4.

Referring to FIG. 5, one embodiment of a method 120 of preparing a site is depicted. First, at least one pit is dug into the ground at the site in block 122. The pit must be deep enough to detect the depth of the water table. Preferably, the pit is deep enough to contain water when the water table is at its greatest depth. In one embodiment, a suitable depth is 18 inches.

Next, at block 124, at least one water-level probe is placed in each pit to detect the depth of the water table. Each water-level probe may be connected to an automatic data collection device. Alternatively, manual recordation can be taken from the measurements of each water-level probe. In one embodiment, water-level probes capable of accurately detecting the depth of the water table to within one tenth of an inch are used. However, any suitable water-level probe may be used. Non-limiting examples of suitable water-level probes include pressure transducers available in stainless steel configurations, water-level probes wherein the changing water-level turns a potentiometer, and water-level probes wherein water-levels are detected from the pressure of air bubbled into the water. Air bubbling probes may consist of an air hose inside a sturdy tube for insertion into the ground. A flange on the tube controls the depth of insertion. A pressure generator such as an aerator pump may be connected to the tube to supply air. Preferably, the pressure generator is located inside an enclosure.

Next, in block 126, a precipitation meter is placed at the site to periodically measure the amount of precipitation. The precipitation meter may be connected to an automatic data collection device. Alternatively, manual readings may be taken from the precipitation meter. Suitable meters include rain gauges or other devices for measuring the amount of precipitation known in the art. Particularly, water-level probes similar to those discussed above may be used inside a hopper for collecting water provided a means for periodically emptying the water from the hopper is included. In one embodiment, an automatic means of emptying the water from the hopper is provided.

In block 128, both air and soil temperature probes are installed at the site. The temperature probes may be connected to an automatic data collection device or the temperature measurements may be taken manually. Any suitable temperature probe known in the art may be used. Non-limiting examples of suitable temperature probes include commonly available resistant temperature detectors (RTDS) and thermocouple probes. At block 129, the site setup method 120 terminates.

Optionally, a hygrometer may be installed to measure humidity at the site. Any suitable hygrometer known in the art may be used. The hygrometer may be connected to an automatic data collection device or the humidity measurements may be taken manually.

Returning to FIG. 4, after the site has been setup in block 120, the method 100 begins collecting data at block 130. As mentioned above, the various probes may be connected to an automatic data collection device. Further, the data collected automatically may be communicated to another location for further analysis.

Figure 6:
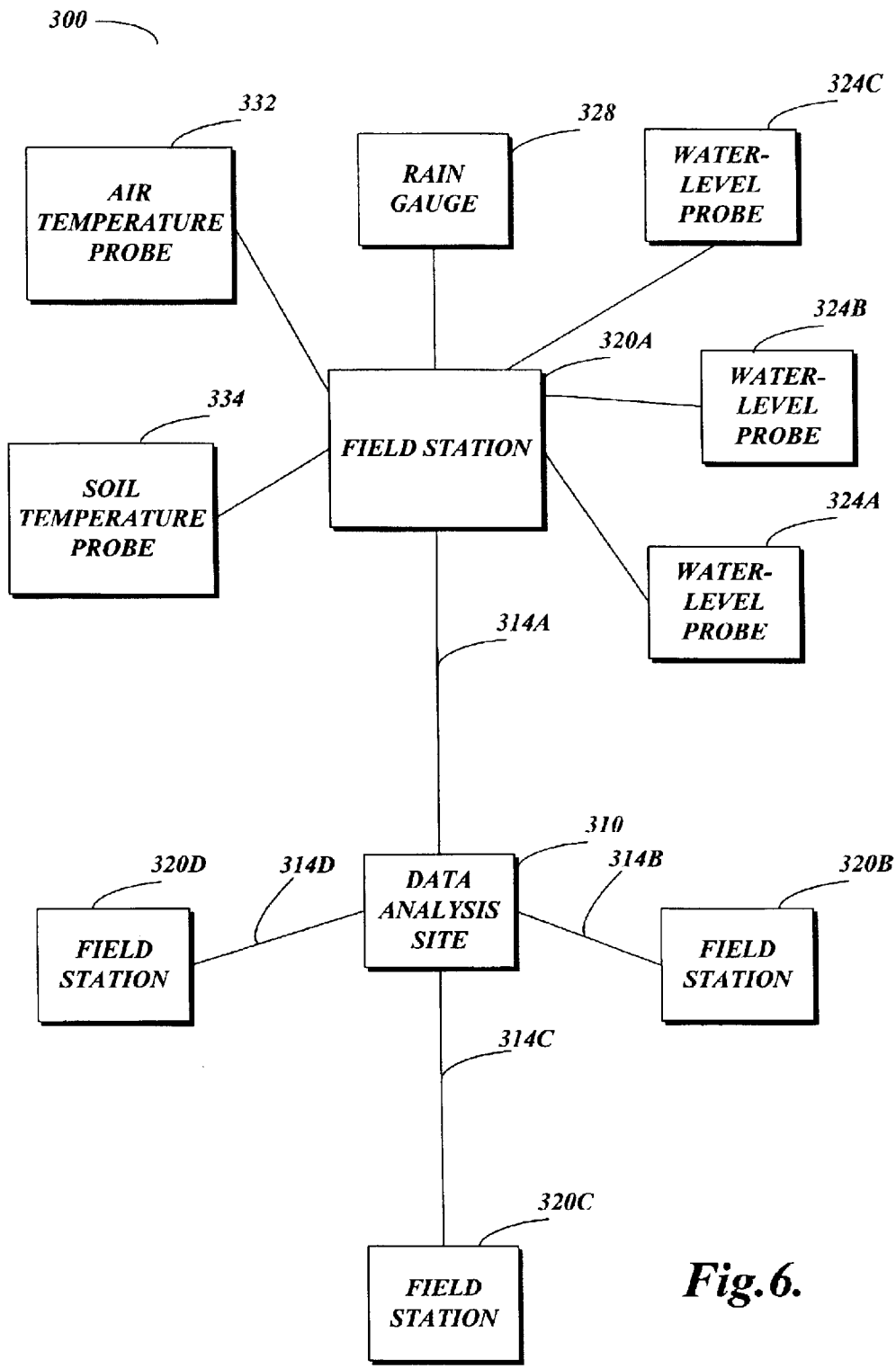
FIG. 6 is a block diagram depicting a system for collecting site data and analyzing site data in accordance with the method of FIG. 4.

Referring to FIG. 6, a system 300 for automatically collecting data from the site setup of block 120 is depicted. Each site selected may include a field station 320. Exemplary field station 320A includes three water-level probes 324A, 324B, and 324C. While three water-level probes are depicted, it is apparent to one of ordinary skill in the art that more or fewer water-level probes may be used. Field station 320A also includes a rain gauge 328, an air temperature probe 332, and a soil temperature probe 334. Some or all of the probes may be connected to an automatic data collection device. Field stations 320B, 320C, and 320D may include probes similar to those of field station 320A.

Figure 7:
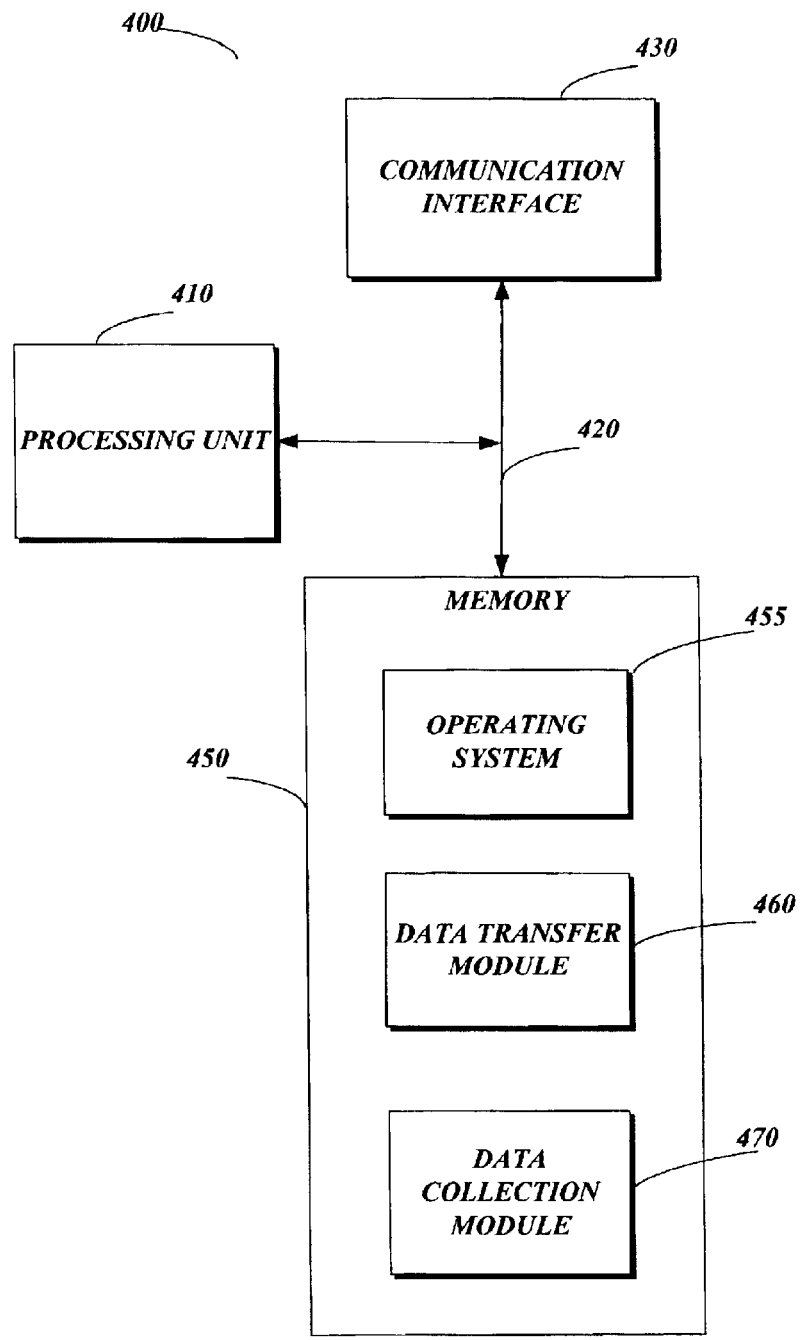
FIG. 7 is a block diagram depicting an illustrative architecture of a data collection device for use with the system of FIG. 6.

Referring to FIG. 7, a data collection 400 device suitable for automatically collecting data from some or all of the water-level probes, rain gauge, air temperature probe, and soil temperature probe is depicted. If automatic data collection is desired, each field station 320 may be equipped with a data collection device 400. Data collection device 400 includes a processing unit 410 coupled to a memory 450 via a bus 420. Other peripheral devices may also be connected to the processor in a similar manner.

Optionally, data collection device 400 may include a communication interface 430 coupled to the processing unit 410 via bus 420. Communication interface 430 may include a cellular telephone modem or other telecommunication or computer communication device known in the art that is capable of transmitting data to the data analysis site 310 (shown in FIG. 6). The communication interface 430 may include a modem for connecting directly to a computer, another data collection device 400, or to an Internet service provider through a Point-to-Point Protocol ("PPP") connection or a Serial Line Internet Protocol ("SLIP") connection as known to those skilled in the art. The modem may utilize a telephone link, cable link, wireless link, Digital Subscriber Line or other types of communication links known in the art. In another embodiment, the communication interface 430 may include a network interface for connecting directly to a LAN or a WAN, or for connecting remotely to a LAN or WAN. Those of ordinary skill in the art will appreciate that the communication interface includes the necessary circuitry for such a connection, and is also constructed for use with various communication protocols, such as the TCP/IP protocol, the Internet Inter ORB Protocol ("IIOP"), and the like. The communication interface 430 may utilize the communication protocol of the particular network configuration of the LAN or WAN it is connecting to, and a particular type of coupling medium.

Memory 450 may include operating system 455, a data transfer module 460, and a data collection module 470. The operating system 455 may control the operation of the data collection device 400. Data transfer module 460 includes all of the code and commands necessary to transfer data from the data collection device 400 to the data analysis site 310 via the communication link 314. Data collection module 470 includes all of the code and commands necessary to receive measurements from the various probes connected to data collection device 400. Additionally, data collection module 470 may include code for converting the signals received from the field probes for data transfer or to place them in a format that is more easily accessible by users or other software programs.

Figure 8:
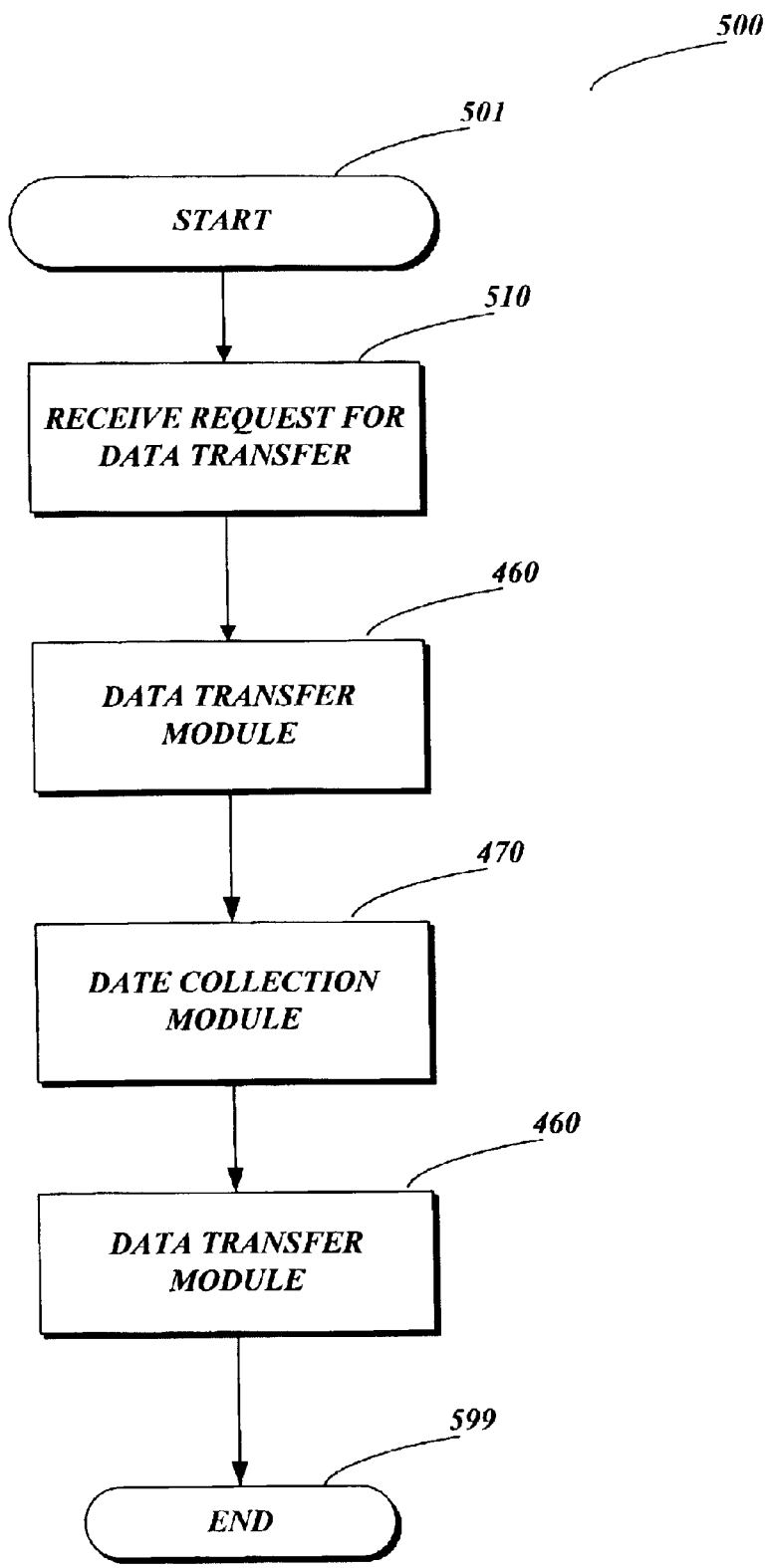
FIG. 8 is a flow diagram illustrative of a data collection method implemented by the data collection device of FIG. 7.

FIG. 8 depicts one embodiment of a method 500 that the data collection device 400 may use to collect and transmit data. In one embodiment, the data analysis site 310 may send a request to transfer data to the field station 320. Referring to FIG. 8, when the data collection device 400 receives a request to transfer data at block 510, the data transfer module 460 receives the request. Next, the data collection module 470 obtains the measurements from the various probes. At this point, the data collection module 470 may need to convert or compress the data for transfer. The data collected is then transferred over communication link 314 to the data analysis site 310 by the data transfer module 460.

Alternatively, data collection device 400 may include a data recordation module that includes the computer-readable components required to record measurements taken from the various probes in memory 450. Memory 450 may include removable media such as removable storage drives, writable CDs, and floppy discs that can be removed and transferred to another location such as data analysis site 310. In another embodiment, data collection device 400 may include a data communication interface that allows a user to download data stored in memory 450 directly to another device or external memory. In this embodiment, data can be analyzed on site or transferred elsewhere.

Data collection device 400 may be located inside an enclosure or may include its own water-tight housing. The power supply for data collection device 400 may include solar panels, micro wind turbines, and/or batteries. Alternatively, if data collection device 400 is located inside an enclosure, the device may be connected to a typical electrical wall outlet. While a standard personal computer may perform the functions of data collection device 400, a computer is not necessarily required, other devices such as programmable logic controllers and embedded systems may be used to collect and transmit the data collected.

It may be beneficial to connect more than one field station 320 to a centralized data analysis site 310. As depicted in FIG. 6, multiple field stations 320A, 320B, 320C, and 320D, may be connected to data analysis site 310 via communications links 314A, 314B, 314C, and 314D, respectively. In this manner, as the data collection device 400 at each field station collects data, it may be transferred to data analysis site 310. Data analysis site 310 may include a computing device 600 for receiving and analyzing data from the field stations 320.

Figure 9:
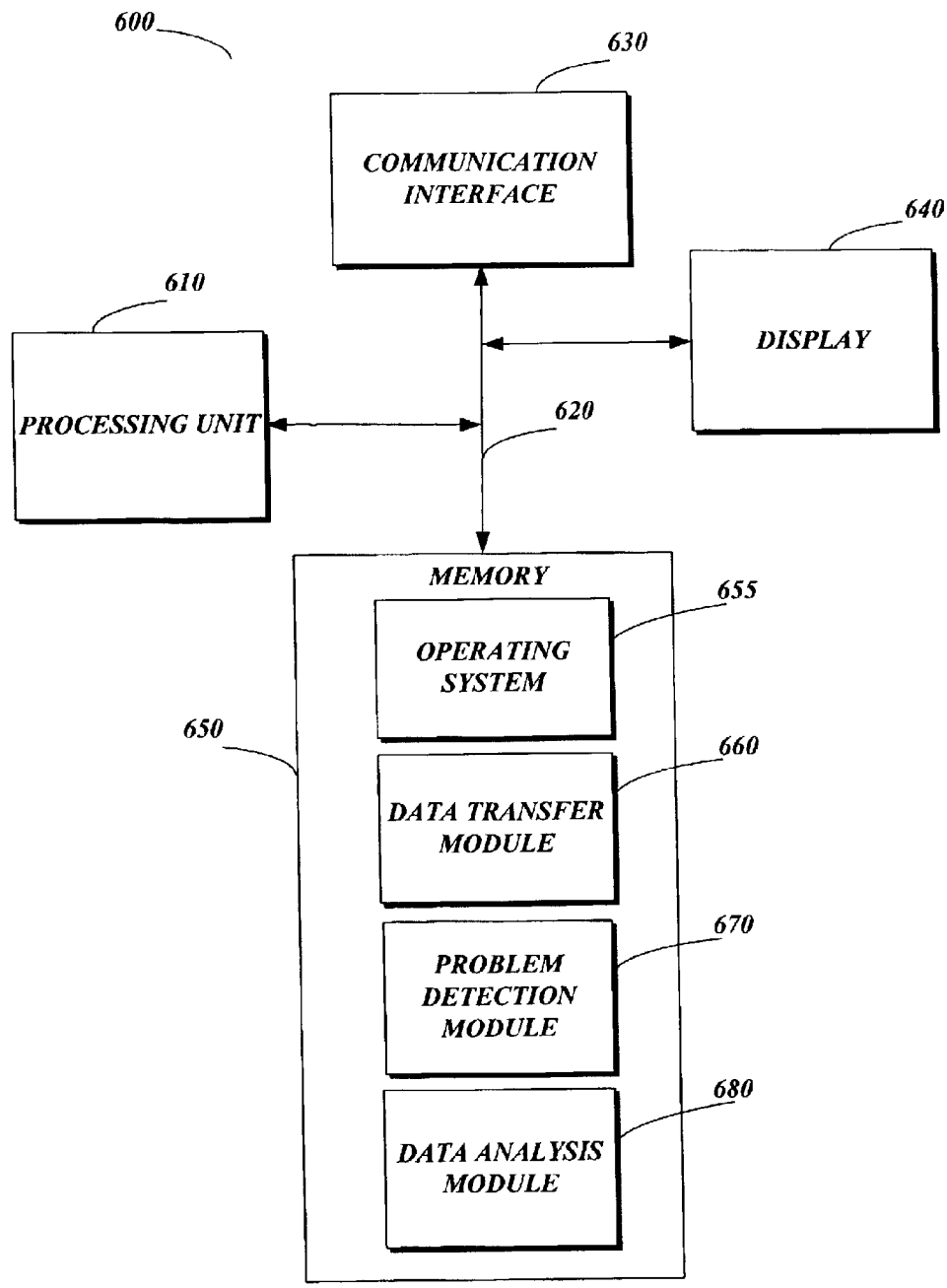
FIG. 9 is a block diagram depicting an illustrative architecture of a computing device capable of implementing a method of determining the depth to the saturated soil in accordance with the method of FIG. 4.

In one embodiment, the data analysis site 310 includes a computing device 600, such as a personal computer. FIG. 9 depicts several of the key components of the computing device 600. Those skilled in the art will appreciate that the computing device includes many more components than are shown in FIG. 9. However, it is not necessary that all of these generally conventional components be shown in order to disclose an enabling embodiment for practicing the present invention.

The computing device 600 includes a processing unit 610, a display 640, and a memory 650. The memory 650 generally comprises a random access memory ("RAM"), a read-only memory ("ROM"), and a permanent mass storage device, such as a hard disk drive, tape drive, optical drive, floppy disk drive, CD-ROM, DVD-ROM, or removable storage drive. The memory 650 stores an operating system 655 for controlling the operation of the computing device 600. The memory may also store the data transfer module 660, problem detection module 670, and data analysis module 680 of the present invention. It will be appreciated that the operating system 655 and aforementioned modules may be stored on a computer-readable medium and loaded into memory 650 of the computing device 600 using a drive mechanism associated with the computer-readable medium, such as a floppy, CD-ROM, DVD-ROM drive, or network interface. The memory 650 and display 640 are connected to the processor 610 via a bus 620. Other peripherals may also be connected to the processor in a similar manner.

As shown in FIG. 9, in one embodiment of the invention, the computing device 600 may include a communication interface 630 coupled to the processor 610 for establishing a communication link with external computers and computing networks. The communication interface 630 may include a modem for connecting directly to another computer, the data collection device 400, or to an Internet service provider through a Point-to-Point Protocol ("PPP") connection or a Serial Line Internet Protocol ("SLIP") connection as known to those skilled in the art. The modem may utilize a telephone link, cable link, wireless link, Digital Subscriber Line or other types of communication links known in the art. In another embodiment, the communication interface 630 may include a network interface for connecting directly to a LAN or a WAN, or for connecting remotely to a LAN or WAN. Those of ordinary skill in the art will appreciate that the communication interface includes the necessary circuitry for such a connection, and is also constructed for use with various communication protocols, such as the TCP/IP protocol, the Internet Inter ORB Protocol ("IIOP"), and the like. The communication interface may utilize the communication protocol of the particular network configuration of the LAN or WAN it is connecting to, and a particular type of coupling medium.

Memory 650 may include a data transfer module 660 for receiving data from each field station 320 via communications link 314. In one embodiment, memory 650 also includes a problem detection module 670. Problem detection module 670 includes computer code and components necessary to detect when the data received from a particular field station 320 contains errors. For example, if a quick movement of the water-level occurs without the onset of a rainstorm, there may be a problem in the system. Additionally, the problem detection module 670 may alert a user if a particular field station is not transmitting all of the data it should be collecting.

Additionally, memory 650 may include a data analysis module 680. Data analysis module 680 may include all of the calculations, functions, and computer code necessary to perform the method of determining the depth to the saturated soil of the present invention. The method 140 of determining the depth to the saturated soil will be described in greater detail below with reference to FIG. 11.

Figure 10:
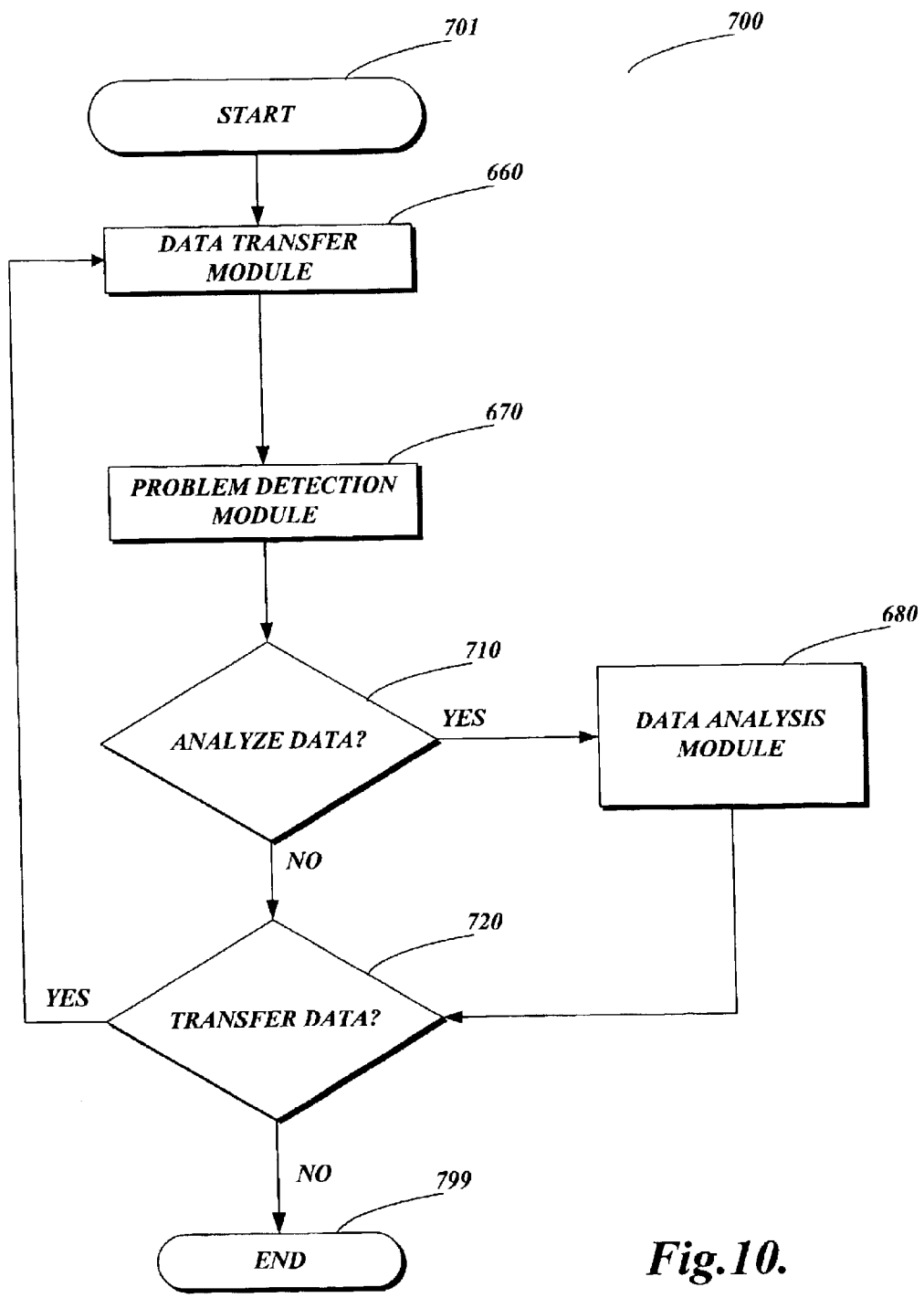
FIG. 10 is a flow diagram illustrative of a data transfer and analysis method implemented by the computing device of FIG. 9 in accordance with the present invention.

Referring to FIG. 10, one embodiment of a method by which the computing device 600 may receive and analyze data is depicted. The method 700 starts at block 701. Next, the data transfer module 660 requests data from at least one field station 320. In one embodiment, such requests occur automatically every 120 seconds. After data is received, the problem detection module 670, examines the data and determines whether to issue a warning of a problem with the data. At decision block 710, the user decides whether to analyze data. If the user wishes to analyze data, the data analysis module 680 performs the analysis. If the user decides not to analyze data or has finished analyzing data, the user decides whether to transfer additional data at decision block 720. If the user wishes to transfer additional data, the method 700 returns to the data transfer module 660. Otherwise, the method 700 terminates at block 799.

Figure 11:
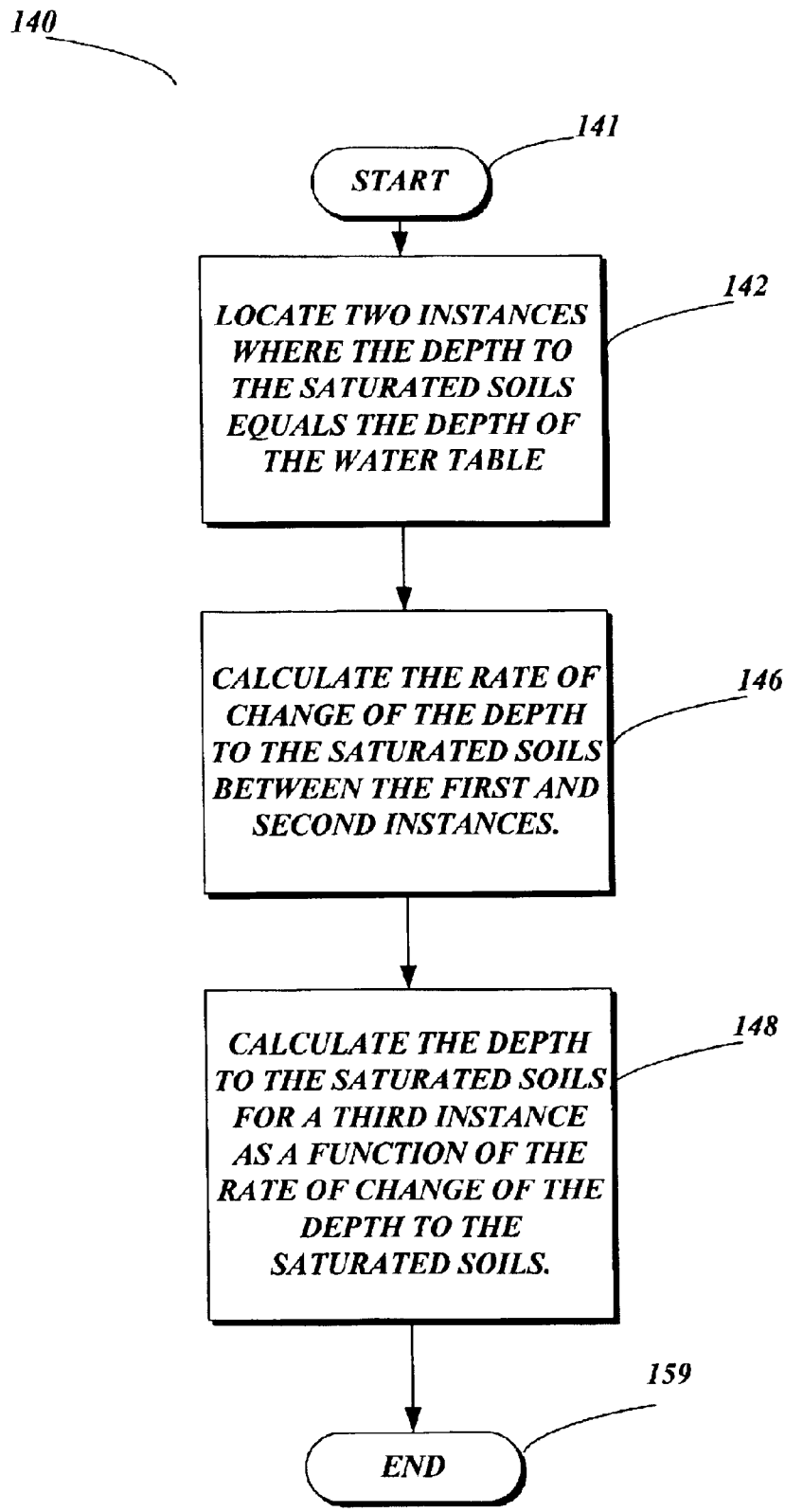
FIG. 11 is a flow diagram illustrative of a method of determining the depth to the saturated soil in accordance with the method of FIG. 4.

After sufficient data has been collected in block 130, the data may be analyzed to determine the depth to the saturated soil in the ground at a particular site in block 140. Referring to FIG. 11, the method 140 for analyzing the data collected is illustrated in greater detail. This method may be performed manually or by automatic means such as data analysis module 680. The method 140 starts at block 141. Two instances where the depth to the saturated soil equals the depth of the water table are selected as a first and second instance in block 142. Preferably, there are no instances in which the depth to the saturated soil equals the depth of the water table occurring between the first and second instance.

An instance where the depth to the saturated soil equals the depth of the water table can be identified in at least three ways. First, whenever the water table is at the surface of the soil, the depth to the saturated soil is also at the surface of the soil. Second, whenever the water table is above the surface of the soil, the depth to saturated soil is also above the surface of the soil. Lastly, whenever there is sufficient rain, the depth of the water table will rise rapidly to equal the depth to the saturated soil. Therefore, a rapid rise in the depth of the water table coinciding with rain fall may signify that the depth of the water table and the depth to saturated soil are equal. Therefore, instances identified as occurring during at least these three circumstances may be used as the first and/or second instances.

In block 146, the rate of change of the depth to the saturated soil is calculated between the first and second instances. The rate of change of the depth to the saturated soil may be calculated as a function of the amount of time between the first and second instances, the depth of the water table at the first and second instances, the total precipitation occurring between the first and second instances, and the specific yield of the soil at the site. Specifically, the rate of change of the depth to the saturated soil may be calculated as follows. First, the total precipitation occurring between the first and second instances is divided by the specific yield of the soil at the site to obtain offset $\alpha$. Because determining specific yield may be difficult, an assumed value such as 0.3 may be used. If an assumed or initial value is used, the value may be modified later as more data is collected to better reflect water depletion at the site. Next, offset $\alpha$ is added to the depth of the water table at the second instance and the depth of the water table at the first instance is subtracted from that sum to obtain depth $\beta$. Then, depth $\beta$ is divided by the amount of time between the first and second instances to obtain the rate of change of the depth to the saturated soil. In some embodiments, it may be beneficial to measure time in periods that are easily graphed. In those embodiments, depth $\beta$ may simply be divided by the number of periods between the first and second instances to acquire the rate of change of the depth to the saturated soil. The rate of change value may be stored such as in memory 650 for future use.

In block 148, the depth to the saturated soil is calculated for an instance occurring between the first and second instances. On a hydrograph, where the X-axis is time and the Y-axis is depth, the first and second instances and the depth of the water table at those instances may be plotted. By drawing a line from the first instance with a slope equal to the rate of change of the depth to the saturated soil, the depth to the saturated soil can be estimated for instances occurring after the first instance and before the second instance. In other words, a linear model of the depth to the saturated soil can be produced. While in reality depletion mechanisms such as drainage, evaporation, and/or transpiration may not deplete the water from the ground linearly, a linear model offers a reasonably close approximation of the depth to the saturated soil. However, as more data is collected, it may be desirable to use the data collected to calculate a non-linear model of the rate of change of the depth to the saturated soil.

In the preferred embodiment, the linear model is adjusted to include the effects of precipitation occurring at the site. The adjustment is based on the general principles of conservation of mass. After an instance between the first and second instances is selected, the adjustment is calculated by totaling all of the precipitation occurring from the first instance, to and including the precipitation occurring on the selected instance. Using the depth of the water table at the first instance and the rate of change of the depth to the saturated soil, the unadjusted predicted depth to the saturated soil may be obtained. Then, the adjustment (i.e., the total precipitation occurring from the first instance to and including the precipitation occurring on the selected instance) may be added to the unadjusted predicted depth. On a hydrograph, like the one discussed above, the adjustment may be depicted at the periods where precipitation occurred. Specifically, at a period where rain occurred, the linear model may be "stepped up" by an amount corresponding to the amount of precipitation that occurred on that period. In one embodiment, the depth of the linear model is simply stepped up (or moved closer to the surface of the soil) by an amount equal to the amount of precipitation occurring on that period. This may give the hydrograph a saw-toothed appearance.

Figure 12A:
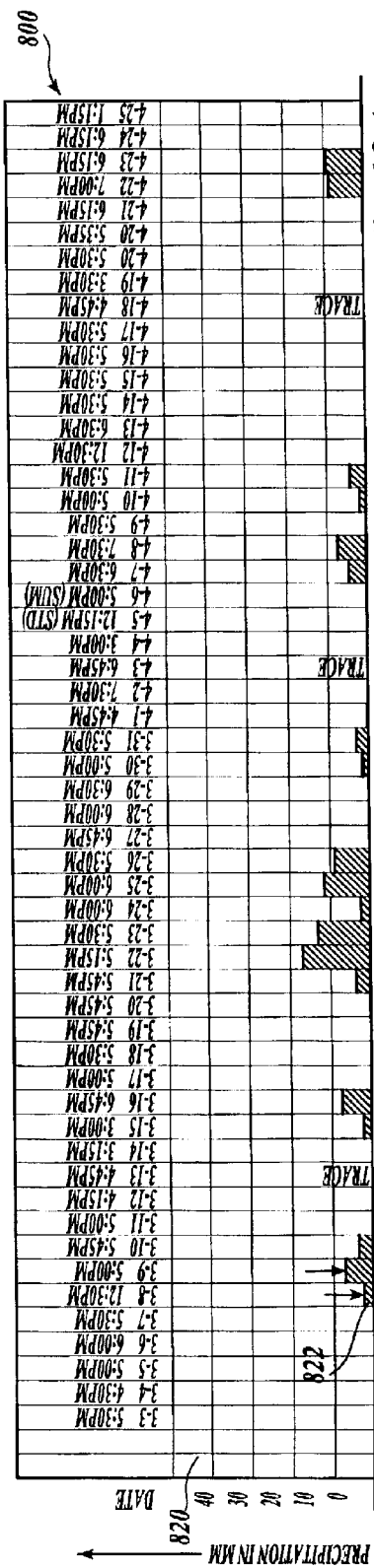
FIG. 12A is an exemplary graph of precipitation occurring periodically at a selected site.
Figure 12B:
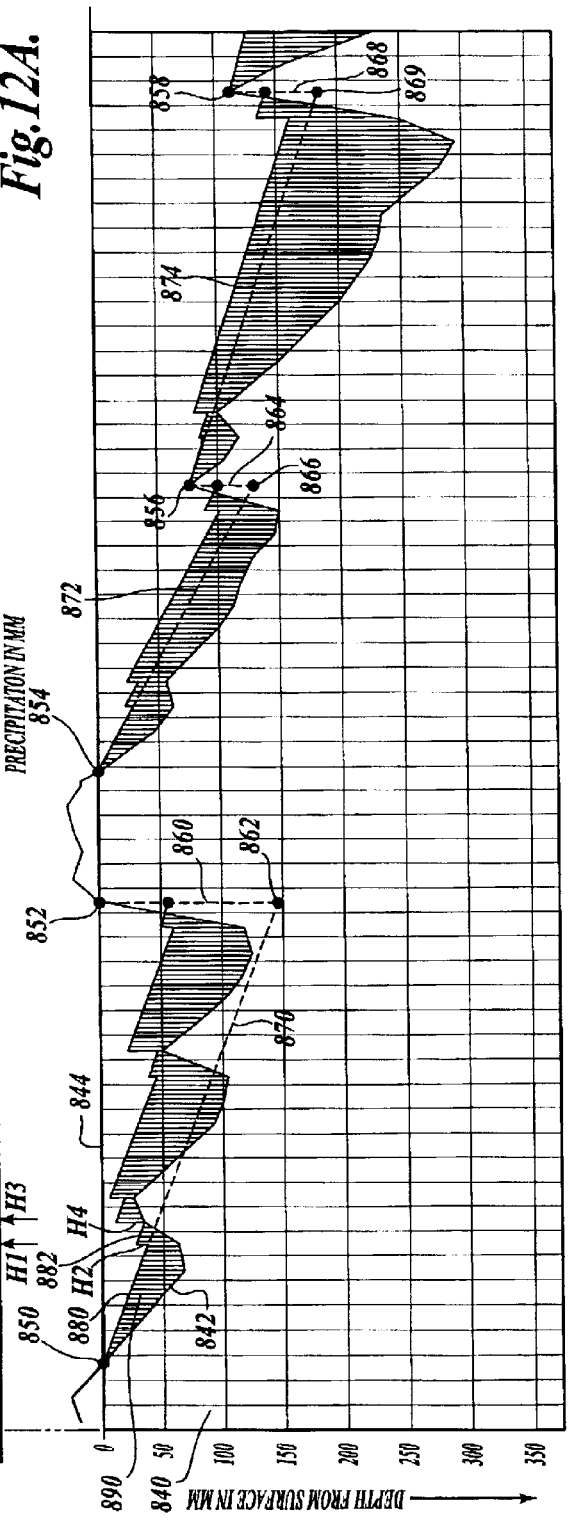
FIG. 12B is an exemplary hydrograph constructed using the method of FIG. 11.

FIGS. 12A and 12B illustrate a hydrograph constructed in accordance with the present invention. FIG. 12A depicts a precipitation graph 820. This graph may be useful to determine the total precipitation between the various instances and the periods at which precipitation occurred.

Referring to FIG. 12B, a non-limiting example of a hydrograph produced in accordance with the present invention is provided for illustrative purposes. Hydrograph 840 includes two instances 850 and 852 where the depth to the saturated soil equals the depth of the water table because at both the first instance 850 and the second instance 852 the water table was at the surface of the soil 844. Consequently, points 850 and 852 represent instances where both the water table 842 and the depth to the saturated soil were at the surface of the soil 844. It is preferred to use instances where the water table and the depth to the saturated soil are at the surface of the soil because this fact can be easily verified either visually or by water-level probes. The water-level probes 324 located at each field station 320 may be used to measure the depth of the water table over time. On hydrograph 840, the depth of the water table over time is depicted as line 842. The offset α was calculated as described above and is depicted as line 860. The offset α was then added to the depth of the water table at the second instance to obtain point 862. Next, the rate of change of the depth to the saturated soil is depicted as the slope of line 870 extending from the first instance 850 to point 862. In other words, the rate of change of the depth to the saturated soil can be determined by connecting the first instance to a point located offset distance α below the second instance.

As can be seen in hydrograph 840, the linear model (i.e., line 870) is not the best predictor of the depth to the saturated soil because in several locations, the line 870 passes beneath the water table. In reality, the depth to the saturated soil is always at or above the depth of the water table. Therefore, adjustments based on precipitation may be necessary.

The periodic amounts of precipitation measured by the precipitation meter 328 are depicted in the precipitation graph 820. To adjust the hydrograph, periods in which precipitation occurred between the first and second instances must be identified. In one embodiment, periods in which only trace amounts of precipitation occurred may be ignored. Ignoring periods with trace amounts of precipitation, there are six periods between the first 850 and second 852 instances in which precipitation occurred: March 8, March 9, March 10, March 15, March 16, and March 21. On each of these periods, the adjusted linear model 880 representing the depth to the saturated soil is stepped up by the amount of precipitation occurring on the period. Specifically, referring to March 8, a vertical line with a length H2 equal to the amount of precipitation H1 that fell on Mar. 8, 1998, is drawn from the intersection of the middle of Mar. 8, 1998, and line 870. The linear model is then continued until the next period with rain is encountered, where an adjustment may again be performed. These steps are repeated until the hydrograph reaches the second instance 852.

After the second instance 852 is reached, the data analysis process 140 may be repeated for the next pair of instances where the depth of the water table equaled the depth to the saturated soil. Referring to FIG. 12B, the next pair of instances may include 852 and 854; 854 and 856; or 856 and 858. It is important to note that the depth of the water table was above the surface of the soil the entire time between instances 852 and 854. Therefore, the data analysis method 140 need not be performed on this pair of instances.

Referring to FIG. 12B, it can be observed that in two instances 856 and 858 the depth to the saturated soil equaled the depth of the water table below the surface of the soil. These instances may be treated the same as instances where the water table is at the surface of the soil. Further, these instances may be used to test the accuracy of the hydrograph. If the hydrograph predicted the depth of the water table would equal the depth to the saturated soils within a reasonable degree of error, the model may not require adjustment. However, if the degree of error is too large, the rate of change of the depth to the saturated soil may be modified or a non-linear rate of change applied. As a non-limiting example, an error of up to one inch may be used.

In one embodiment of the present invention, the rate of change of the depth to the saturated soil is calculated for each pair of instances selected. For example, the slope of line 872 represents the rate of change of the depth to the saturated soil between instances 854 and 856. Referring to FIG. 12B, it may be observed that the slope of line 870 does not equal the slope of line 872.

The rate of change of the depth to the saturated soil can be used to predict future the depths of the saturated soil. Further, the rate of change can be averaged over time to create a more accurate prediction of the depth to the saturated soil. In other words, because the rate of change of the depth to the saturated soil corresponds to the rate at which water is depleted from the site, the rate of change of the depth to the saturated soil can be used as a predictor of the rate of future water depletion from the site. Additionally, the total amount of precipitation occurring from the second instance, to and including the precipitation occurring on the future instance may be used to adjust the predicted depth to saturated soil at the future instance.

Generally, the rate of depletion may be affected by several factors. Specifically, at least the following factors may affect the rate of depletion: the depth to the saturated soil, the temperature of the soil, the temperature of the air, humidity, seasonal changes in vegetation, in flow of water from the watershed above the site, and outflow of the water to areas downstream of the site. Because the depletion rate may vary with these factors, these factors may be correlated with the rate of change of the depth to the saturated soil to create improved predictions or a set of depletion characteristics. For example, referring to FIG. 12B, the slope of line 870 is less than the slope of line 872. This difference in slope may be the result of one or more of the factors that affect the rate of depletion. Therefore, correlating each of these slopes with one or more of the factors that affect the rate of depletion may improve the model (hydrograph) of the site. The rate of change of the depth to the saturated soil and any correlations with other information or factors may be stored such as in memory 650 for future use.

Because several of the above factors may vary over time and with the seasons, the depletion rate may also vary over time. Therefore, it may be beneficial to determine one or more depletion rates over the course of a year or for several years. In other words, data collected over time may be used to create an improved set of depletion characteristics for a site that may be used to determine and predict the depth to the saturated soil.

Additional circumstances may also effect the depletion rate. For example, changes to the topography or surface water of surrounding lands may change the depletion characteristics of a site. Therefore, sites may require occasional reevaluations or continuous monitoring. Particularly, sites that border on being considered wetlands may benefit from such measures.

Figures 13A, 13B:
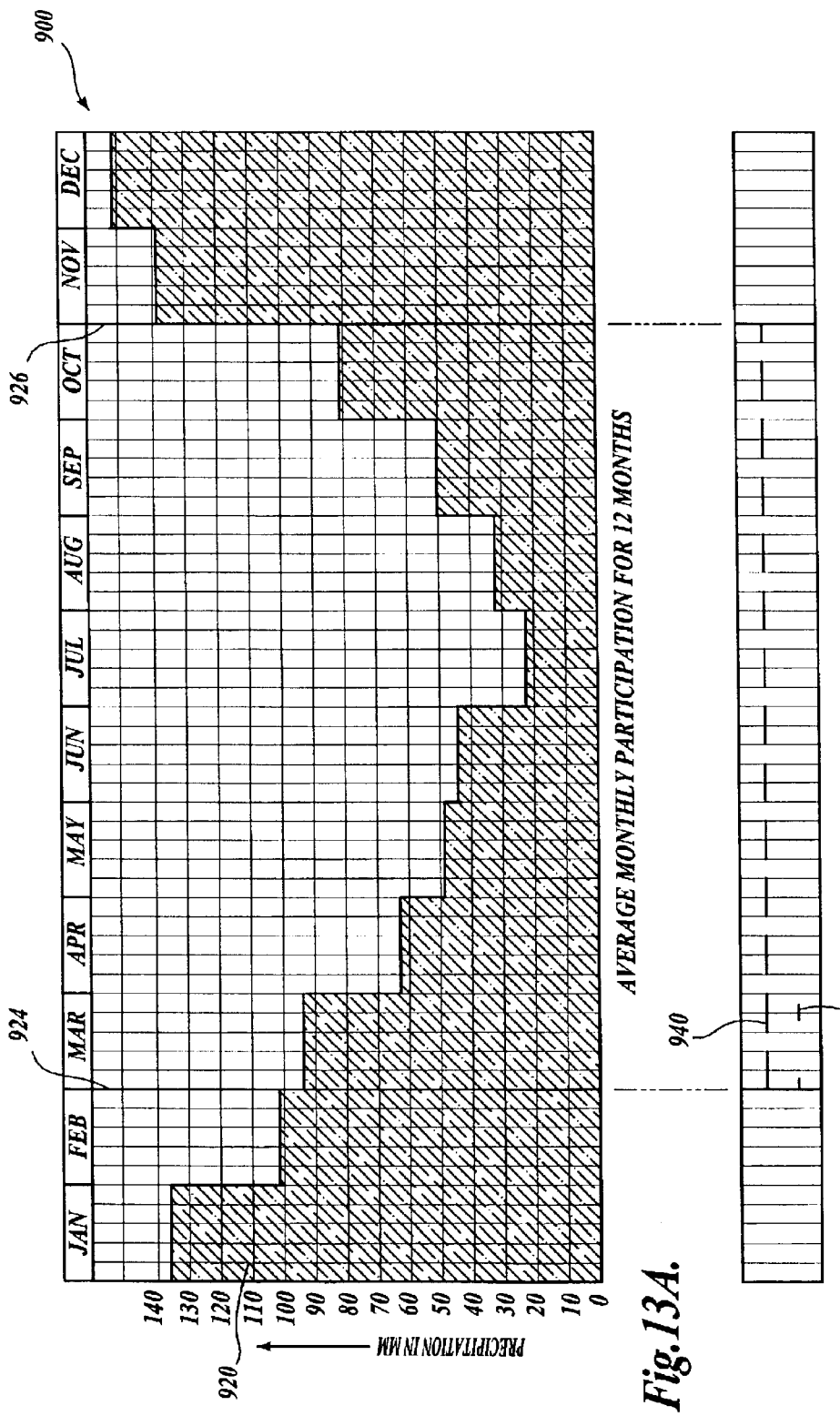
FIG. 13A is an exemplary graph of precipitation occurring at the selected site.
FIG. 13B is an exemplary graph depicting the '87 Manual standard for a wetland at the selected site and the duration of time the soil was saturated to the surface at the selected site as determined using the method of FIG. 11.

Returning to FIG. 4, after the analysis of data has completed, the results can be compared with standards to determine whether a site qualifies as a wetland in block 170. Referring to FIGS. 13A and 13B, an example of such of comparison is depicted. FIG. 13A depicts the average monthly precipitation occurring in a 12 month period at a specific site. Area 920 illustrates the average precipitation occurring each month. Line 924 indicates the start of the growing season and line 926 indicates the end of the growing season.

FIG. 13B illustrates a time-span graph depicting two data sets. The horizontal lines 940 and 950 illustrate the time-spans of each data set. Lines 940 illustrate the first data set. The first data set is constructed from an interpretation of text of the '87 Manual and depicts a permissible pattern of saturation to the surface of the soil that can occur before a site is a wetland. None of the time-spans depicted as lines 940 equal 5% of the growing season.

The second data set is the amount of time during the growing season that the soil at a particular site was saturated to the surface. Lines 950 illustrate the periods during March that hydrograph 840 demonstrated that the surface of the soil was saturated. Specifically, lines 950 correspond to the period before and up to instance 850 and the period between instances 852 and 854 of FIG. 12B. FIG. 13B clearly illustrates that none of the lines 950 continuously occupy 5% of the growing season. Therefore, according to the '87 Manual, the site depicted in FIGS. 12A–13B is not a wetland.

Returning to FIG. 4, in decision block 180, a decision is made whether to continue monitoring the site. If monitoring is continued, method 100 returns to collecting data in block 130. If monitoring is not continued, the setup is removed from the site at block 190 and the method terminates at block 199.

The method described herein and the system for implementing the method provide an objective means by which the depth to the saturated soil may be determined. It may be desirable to adjust the calculation parameters, such as specific yield, to achieve a particular level of accuracy. For example, it may be desirable to achieve an accurate prediction of the depth to the saturated soil up to one inch.

As mentioned above, it may be desirable to correlate the rate of change of the depth to the saturated soil with the factors that affect water depletion. In this manner, a set of depletion characteristics can be obtained that may be used to improve the accuracy of the determination and/or prediction of the depth to the saturated soil.

The system removes much of the necessity to make numerous visits to the site. Further, the system provides an opportunity to measure the depth to the saturated soil continuously over a long duration of time including more than one growing season. The more data collected the more accurate the hydrograph may become as it is refined over time because the accuracy of predictions based on the hydrograph can be verified with the next rainfall and the depletion characteristics (including the rate of change of the depth to the saturated soil) adjusted accordingly. Additionally, factors that vary over time may be considered to create a hydrograph that includes variation created by such factors.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of determining a depth to the saturated soil above the depth of the water table in the ground at a selected site comprising:
   a. identifying a first instance and a second instance wherein a depth of the water table equals a depth to the saturated soil at the selected site and the second instance occurs after the first instance;
   b. determining the depth of the water table at the first and second instances at the selected site;
   c. determining a total precipitation that occurred between the first and second instances at the selected site;
   d. calculating a rate of change of the depth to the saturated soil as a function of
      i. a specific yield value for the selected site,
      ii. an amount of time between the first and second instances,
      iii. the total precipitation that occurred between the first and second instances, and
      iv. the depth of the water table at the first and second instances;
   e. selecting a third instance; and
   f. calculating a depth to the saturated soil for the third instance as a function of the rate of change of the depth to the saturated soil.

2. The method of claim 1, wherein the third instance occurs between the first and second instances.

3. The method of claim 1, comprising determining the total precipitation that occurred between the first and third instances at the selected site, determining a total amount of precipitation occurring on the third instance at the selected site, and adjusting the depth to the saturated soil for the third instance as a function of the total precipitation that occurred between the first and third instances and the total amount of precipitation occurring on the third instance.

4. The method of claim 1, comprising determining the total precipitation that occurred between the second and third instances at the selected site, determining a total amount of precipitation occurring on the third instance at the selected site, and adjusting the depth to the saturated soil for the third instance as a function of the total precipitation that occurred between the second and third instances and the total amount of precipitation occurring on the third instance.

5. The method of claim 1, wherein identifying a first instance and a second instance occurring after the first instance wherein the depth of the water table equals the depth to the saturated soil at the selected site comprises identifying at least one instance wherein the depth of the water table is at or above the surface of the soil at the selected site.

6. The method of claim 1, comprising correlating the rate of change of the depth to the saturated soil with a temperature of the soil at the selected site.

7. The method of claim 1, comprising correlating the rate of change of the depth to the saturated soil with a temperature of the air at the selected site.

8. The method of claim 1, comprising correlating the rate of change of the depth to the saturated soil with time.

9. The method of claim 1, comprising correlating the rate of change of the depth to the saturated soil with a humidity at the selected site.

10. The method of claim 1, comprising correlating the rate of change of the depth to the saturated soil with the depth to the saturated soil for the third instance.

11. The method of claim 1, wherein identifying a first instance and a second instance wherein a depth of the water table equals a depth to the saturated soil at the selected site comprises identifying at least one instance where the depth of the water table rapidly rises toward the surface of the soil.

12. A system for determining a depth to the saturated soil in the ground at a selected site, said depth to the saturated soil is above the depth of the water table, said system comprising:
   a. a means for periodically measuring an amount of precipitation at the selected site to obtain a series of precipitation measurements;
   b. a means for storing the series of precipitation measurements;
   c. a means for periodically measuring the depth of the water table at the selected site to obtain a series of depth of water table measurements;
   d. a means for storing the series of depth of water table measurements;
   e. a means for identifying instances within the stored series of depth of water table measurements wherein the depth to the saturated soil equals the depth of the water table; and
   f. a means for determining a rate of change of the depth to the saturated soil between a pair of instances identified as instances where the depth to the saturated soil equals the depth of the water table as a function of a specific yield value for the selected site, a portion of the stored series of precipitation measurements occurring between the pair of instances, and a portion of the stored series of depth of water table measurements corresponding to each instance in the pair of instances.

13. The system of claim 12, comprising a means for calculating a depth to the saturated soil between the pair of instances as a function of the rate of change of the depth to the saturated soil between the pair of instances, the portion of the stored series of precipitation measurements occurring between the pair of instances, and the portion of the stored series of depth of water table measurements corresponding the first of the pair of instances.

14. The system of claim 12, comprising a means for storing the rate of change of the depth to the saturated soil.

15. The system of claim 12, comprising a means for periodically measuring a temperature of the soil at the selected site to obtain a series of soil temperature measurements, a means for storing the series of soil temperature measurements, and a means for correlating the rate of change of the depth to the saturated soil with a portion of the stored series of soil temperature measurements.

16. The system of claim 15, comprising a means for storing the rate of change of the depth to the saturated soil and the correlation between the rate of change of the depth to the saturated soil and the portion of the stored series of soil temperature measurements.

17. The system of claim 12, comprising a means for periodically measuring a temperature of the air at the selected site to obtain a series of air temperature measurements, a means for storing the series of air temperature measurements, and a means for correlating the rate of change of the depth to the saturated soil with a portion of the stored series of air temperature measurements.

18. The system of claim 17, comprising a means for storing the rate of change of the depth to the saturated soil and the correlation between the rate of change of the depth to the saturated soil and the portion of the stored series of air temperature measurements.

19. The system of claim 12, comprising a means for periodically measuring a humidity at the selected site to obtain a series of humidity measurements, a means for storing the series of humidity measurements, and a means for correlating the rate of change of the depth to the saturated soil with a portion of the stored series of humidity measurements.

20. The system of claim 19, comprising a means for storing the rate of change of the depth to the saturated soil and the correlation between the rate of change of the depth to the saturated soil and the portion of the stored series of humidity measurements.

21. The system of claim 12, comprising a means for correlating the rate of change of the depth to the saturated soil with time and a means for storing the correlation between the rate of change of the depth to the saturated soil and time.

22. The system of claim 12, comprising a means for calculating a depth to the saturated soil at an instance not identified as an instance where the depth to the saturated soil equals the depth of the water table as a function of the rate of change of the depth to the saturated soil between the pair of instances.

23. The system of claim 12, wherein identifying instances within the stored series of depth of water table measurements wherein the depth to the saturated soil equals the depth of the water table comprises identifying instances where the depth of the water table rapidly rises toward the surface of the soil.

24. A computer readable medium having computer executable components for implementing a method of determining a depth to the saturated soil above the depth of the water table in the ground at a selected site, the computer executable components comprising computer executable components for:
   a. identifying a first and second instance in which the depth to the saturated soil equals the depth of the water table wherein the second instance occurs after the first instance;
   b. determining a rate of change of the depth to the saturated soil from the first to the second instance; and c. determining a depth to the saturated soil for a third instance as a function of the rate of change of the depth to the saturated soil.

25. The computer readable medium of claim 24, wherein determining the rate of change of the depth to the saturated soil comprises determining the temperature of the air at the selected site.

26. The computer readable medium of claim 24, wherein determining the rate of change of the depth to the saturated soil comprises determining the temperature of the soil at the selected site.

27. The computer readable medium of claim 24, wherein determining the rate of change of the depth to the saturated soil comprises determining the humidity at the selected site.

28. The computer readable medium of claim 24, wherein determining the rate of change of the depth to the saturated soil comprises determining the time of year.

29. The computer readable medium of claim 24, comprising computer executable components for storing the rate of change of the depth to the saturated soil.

30. The computer readable medium of claim 29, wherein determining the rate of change of the depth to the saturated soil comprises retrieving the stored rate of change of the depth to the saturated soil.

31. The computer readable medium of claim 24, comprising computer executable components for modifying the rate of change of the depth to the saturated soil.

32. The computer readable medium of claim 24, comprising computer executable components for determining the total amount of precipitation that occurred at the selected site between the first and second instances, determining the amount of time between the first and second instances, determining a depth of the water table at the selected site at the first and second instances; and determining a specific yield value for the selected site.

33. The computer readable medium of claim 32, wherein determining the rate of change of the depth to the saturated soil from the first to the second instance comprises calculating the rate of change of the depth to the saturated soil as a function of the specific yield value; the amount of time between the first and second instances; the total precipitation that occurred between the first and second instances; and the depth of the water table at the first and second instances.

34. The computer readable medium of claim 24, wherein the third instance is between the first and second instances chronologically.

35. The computer readable medium of claim 24, comprising computer executable components for determining the total amount of precipitation that occurred between the first and third instances, determining the amount of time between the first and third instances, determining the total amount of precipitation that occurred on the third instance, and determining a depth of the water table at the first instance.

36. The computer readable medium of claim 35, wherein the function for determining the depth to the saturated soil for a third instance further comprises the amount of time between the first instance and the third instance, the total precipitation that occurred between the first instance and the third instance, the total precipitation occurring on the third instance, and the depth of the water table at the first instance.

37. A system for determining a depth to the saturated soil in the ground at a selected site, the depth to the saturated soil being above the depth of the water table, said system comprising a data analysis site comprising:

a. a computing device comprising a processing unit and a storage medium coupled to the processing unit, the storage medium storing program code implemented by the processing unit for 1) identifying a first and second instance in which the depth to the saturated soil equals the depth of the water table wherein the second instance occurs after the first instance;

2) determining a rate of change of the depth to the saturated soil from the first to the second instance; and 3) determining the depth to the saturated soil for a third instance as a function of the rate of change of the depth to the saturated soil.

38. The system of claim 37, comprising at least one field station comprising a data collection apparatus comprising a. a processing unit and a storage medium coupled to the processing unit, wherein the storage medium storing program code implemented by the processing unit for determining a depth of the water table and determining an amount of precipitation occurring within a period, b. wherein the field station communicates the depth of the water table and the amount of precipitation occurring within a period to the data analysis site.

39. The system of claim 38, further comprising at least one water-level probe coupled to the data collection apparatus and positioned in the ground to measure the depth of the water table at the selected site.

40. The system of claim 39, wherein determining the depth of the water table comprises acquiring a measurement of the depth of the water table from the at least one water-level probe coupled to the data collection apparatus.

41. The system of claim 38, further comprising a precipitation meter coupled to the data collection apparatus and positioned to measure an amount of precipitation.

42. The system of claim 41, wherein determining an amount of precipitation occurring within a period comprises acquiring a measurement of the amount of precipitation from the precipitation meter coupled to the data collection apparatus.

43. The system of claim 38, comprising a communication interface coupled to the processing unit of the computing device; and a communication interface coupled to the processing unit of the data collection apparatus for communicating with the communication interface of the computing device.

44. The system of claim 43, wherein the storage medium of the computing device comprises program code for receiving the depth of the water table and the amount of precipitation occurring within a period from the data collection apparatus.

45. The system of claim 37, wherein the storage medium of the computing device comprises program code for determining the total amount of precipitation that occurred at the selected site between the first and second instances; determining a depth of the water table at the selected site at the first and second instances; and determining a specific yield for the selected site.

46. The system of claim 45, wherein determining the rate of change of the depth to the saturated soil from the first to the second instance comprises calculating the rate of change of the depth to the saturated soil as a function of the specific yield; the amount of time between the first and second instances; the total precipitation that occurred between the first and second instances; and the depth of the water table at the first and second instances.

* * * * *